US006631021B2

(12) United States Patent
Smith et al.

(10) Patent No.: US 6,631,021 B2
(45) Date of Patent: Oct. 7, 2003

(54) POLYFUNCTIONAL THIIRANE COMPOUNDS

(75) Inventors: Robert A. Smith, Murrysville, PA (US); Michael O. Okoroafor, Export, PA (US); Marvin J. Graham, Monroeville, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 59 days.

(21) Appl. No.: 09/793,886

(22) Filed: Feb. 28, 2001

(65) Prior Publication Data

US 2002/0010313 A1 Jan. 24, 2002

Related U.S. Application Data

(60) Provisional application No. 60/190,635, filed on Mar. 20, 2000.

(51) Int. Cl.$^7$ .............. C08G 75/32; G02F 1/07; C07D 493/00; C07D 495/00
(52) U.S. Cl. .............. 359/241; 359/242; 359/243; 359/244; 522/31; 522/74; 522/168; 522/170; 528/377; 528/378; 528/380; 549/1; 549/90; 549/518; 549/523
(58) Field of Search .............. 522/168, 170, 522/180, 167, 71, 74, 78, 79, 31; 528/293, 377, 378, 380; 348/902; 359/241, 242, 243, 244; 549/1, 90, 518, 523

(56) References Cited

U.S. PATENT DOCUMENTS

| | | | |
|---|---|---|---|
| 3,361,706 A | 1/1968 | Meriwether et al. ........ 260/39 |
| 3,562,172 A | 2/1971 | Ono et al. ............... 252/300 |
| 3,567,605 A | 3/1971 | Becker .................. 204/158 |
| 3,578,602 A | 5/1971 | Ono et al. ............... 252/300 |
| 4,166,043 A | 8/1979 | Uhlmann et al. .......... 252/300 |
| 4,215,010 A | 7/1980 | Hovey et al. ............ 252/300 |
| 4,233,131 A | 11/1980 | Ratcliffe et al. ........ 204/162 |
| 4,342,668 A | 8/1982 | Hovey et al. ............ 252/586 |
| 4,367,170 A | 1/1983 | Uhlmann et al. .......... 252/586 |
| 4,637,698 A | 1/1987 | Kwak et al. ............. 351/163 |
| 4,816,584 A | 3/1989 | Kwak et al. ............. 544/71 |
| 4,818,096 A | 4/1989 | Heller et al. ........... 351/163 |
| 4,826,977 A | 5/1989 | Heller et al. ........... 544/70 |
| 4,880,667 A | 11/1989 | Welch .................. 427/160 |
| 4,931,219 A | 6/1990 | Kwiatkowski et al. ...... 252/586 |
| 4,931,220 A | 6/1990 | Haynes et al. ........... 252/586 |
| 5,066,818 A | 11/1991 | Van Gemert et al. ....... 549/389 |
| 5,238,981 A | 8/1993 | Knowles ................ 524/110 |
| 5,274,132 A | 12/1993 | Van Gemert ............. 549/389 |
| 5,374,668 A | 12/1994 | Kanemura et al. ......... 523/451 |
| 5,384,077 A | 1/1995 | Knowles ................ 252/586 |
| 5,405,958 A | 4/1995 | Van Gemert ............. 544/71 |
| 5,429,774 A | 7/1995 | Kumar .................. 252/586 |
| 5,434,196 A | 7/1995 | Ohkawa et al. ........... 522/100 |
| 5,466,398 A | 11/1995 | Van Gemert et al. ...... 252/586 |
| 5,525,645 A | 6/1996 | Ohkawa et al. ........... 522/74 |
| 5,683,628 A | * 11/1997 | Mizuno et al. |
| 5,708,064 A | * 1/1998 | Coleman et al. .......... 252/582 |
| 5,807,975 A | 9/1998 | Amagai et al. ........... 528/373 |
| 5,932,681 A | 8/1999 | Herold et al. ........... 528/81 |
| 5,942,158 A | * 8/1999 | Okoroafor et al. ........ 252/586 |
| 5,945,504 A | 8/1999 | Amagi et al. ............ 528/373 |
| 5,973,098 A | 10/1999 | Keita et al. ............ 528/65 |
| 5,973,192 A | 10/1999 | Woodbury et al. ......... 560/154 |
| 5,981,616 A | 11/1999 | Yamamura et al. ......... 522/168 |
| 5,985,510 A | 11/1999 | Akutsu et al. ........... 430/269 |
| 6,117,923 A | * 9/2000 | Amagai et al. ........... 523/440 |
| 6,225,439 B1 | * 5/2001 | Amagai et al. ........... 528/377 |

FOREIGN PATENT DOCUMENTS

| | | |
|---|---|---|
| EP | 874016 A2 | 10/1998 |
| EP | 928 802 A2 | 7/1999 |
| EP | 950905 A2 | 10/1999 |
| EP | 0978513 A1 | 9/2000 |
| JP | 62/195383 | 8/1987 |

OTHER PUBLICATIONS

ASTM D–2583–95, Standard Test Method for Indentation Hardness of Rigid Plastics by Means of a Barcol Impressor.
ASTM D–542–95, Standard Test Method for Index of Refraction of Transparent Organic Plastics.
Chemical Abstract 88592b, Jpn. Kokai Tokkyo Koho JP 11 189,592 [99 189,592], Jul. 13, 1999, S. Umeda et al., "Sulfur–containing epoxy compound for thermally stable optical material", vol. 131, 00–00–1999, No. 7.
Chemical Abtract 108723a, Jpn. Kokai Tokkyo Koho Jp 11 183,702 [99 183,702], Jul. 9, 1999, M. Okazaki et al., "(Thio)epoxy resin for plastic lens", vol. 131, 00–00–1999, No. 8.
Chemical Abstract 15407u, Jpn. Kokai Tokkyo Koho JP 11 12,273 [99 12,273], Apr. 28,1989, K. Yamamoto et al., "Episulfides for polymeric optical materials and their preparation", vol 130, 00–00–1999, No. 12.

* cited by examiner

Primary Examiner—Susan W. Berman
(74) Attorney, Agent, or Firm—Carol A. Marmo

(57) ABSTRACT

Describes novel polyfunctional thiiranes. Also described are polymerizable compositions comprising such novel polyfunctional thiiranes, and polymerizates, e.g., optical lenses, prepared therefrom. The described polymerizates may have a refractive index of at least 1.6, and an Abbe number of at least 27.

16 Claims, No Drawings

POLYFUNCTIONAL THIIRANE COMPOUNDS

This application claims the benefit of U.S. provisional application Serial No. 60/190,635, filed Mar. 20, 2000.

DESCRIPTION OF THE INVENTION

The present invention relates to novel polyfunctional thiiranes. The present invention also relates to polymerizable compositions comprising one or more novel polyfunctional thiiranes, and polymerizates, e.g., optical lenses, prepared therefrom.

A number of polymeric materials, e.g., plastics, have been developed as alternatives and replacements for glass in applications such as, optical lenses, fiber optics, windows and automotive, nautical and aviation transparencies. As used herein, the term 'glass' is meant to refer to silica-based inorganic glass. These polymeric materials can provide advantages relative to glass, including, shatter resistance, lighter weight for a given application, ease of molding and ease of dying. Representative examples of such polymeric materials include, poly(methyl methacrylate), thermoplastic polycarbonate and poly[diethylene glycol bis (allylcarbonate)].

The refractive indices of many polymeric materials can be lower than that of glass. For example, the refractive index of poly[diethylene glycol bis(allylcarbonate)] is about 1.50, whereas the refractive index of high index glass can range, for example, from 1.60 to 1.80. When fabricating lenses to correct a given visual defect, e.g., a correction for myopia, the use of a polymeric material having a lower refractive index will require a thicker lens relative to a material having a higher refractive index, e.g., high index glass. If the degree of correction required is substantial, e.g., in the case of severe myopia, a lens fabricated from a low index polymeric material can be so thick as to negate the benefit of reduction in weight obtained by use of a polymeric material. In addition, thick optical lenses are not aesthetically desirable.

It is known that polymeric materials having refractive indices greater than 1.50 can be prepared from monomers containing halogens and/or aromatic rings. However, many such higher index polymeric materials also have undesirably lower Abbe numbers (also known as nu-values). Lower Abbe numbers are indicative of an increasing level of chromatic dispersion, which is typically manifested as optical distortion at or near the rim of the lens.

More recently, polymeric materials, such as optical lenses, having a desirable combination of high refractive indices, e.g., 1.55 or higher, and high Abbe numbers, e.g., at least 27, have been prepared from the thermal polymerization of monomers having episulfide groups (also commonly referred to as thiirane groups). Polymeric materials prepared from the thermal curing of episulfide containing monomers are described in, for example, U.S. Pat. Nos. 5,945,504 and 5,807,975, and European Patent Application Nos. EP 874,016 A2, EP 928,802 A2 and EP 950,905 A2.

It would be desirable to develop new polyfunctional thiirane compounds. It would also be desirable that such newly developed polyfunctional thiiranes be useful as monomers in the preparation of polymerizates, e.g., optical lenses, having a combination of high refractive indices, e.g., refractive inidices of at least 1.6, and adequately high Abbe numbers, e.g., Abbe numbers of at least 27.

In accordance with the present invention, there is provided a polyfunctional thiirane selected from polyfunctional thiiranes represented by the following general formulas:

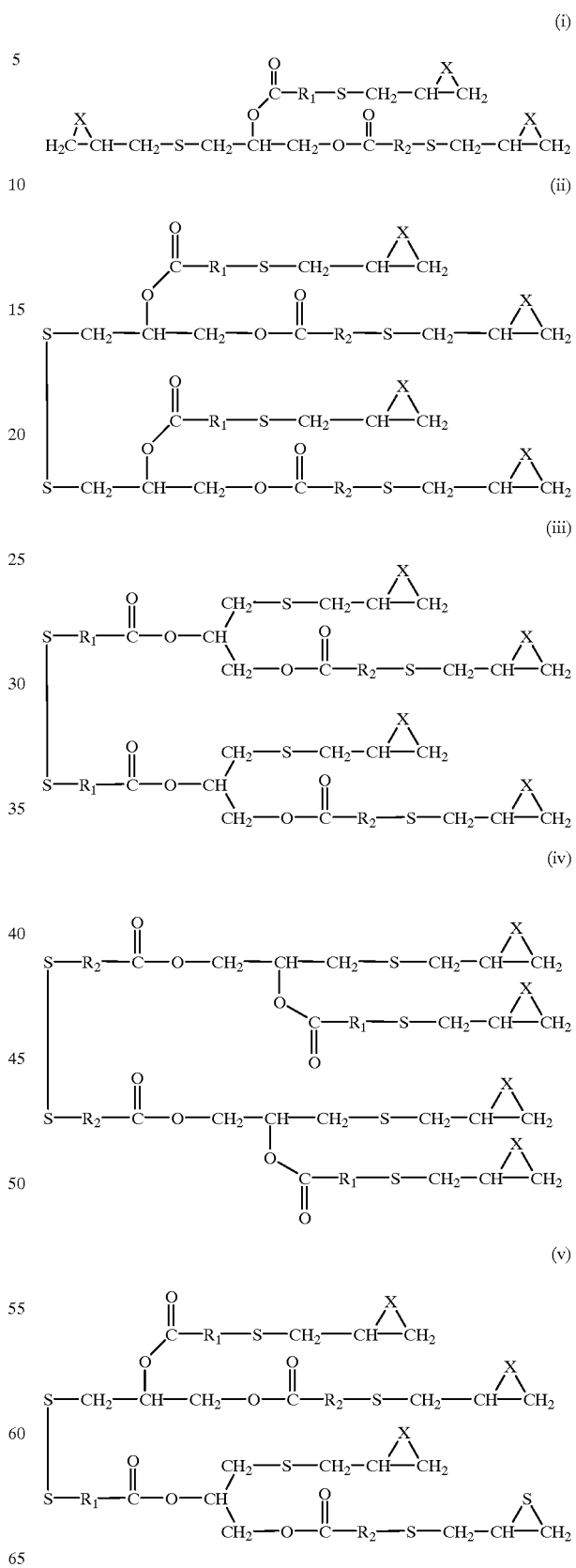

(vi)

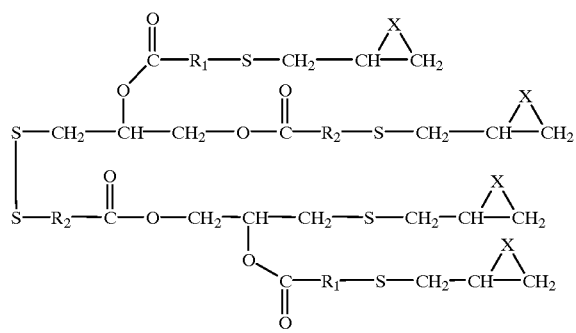

(vii)

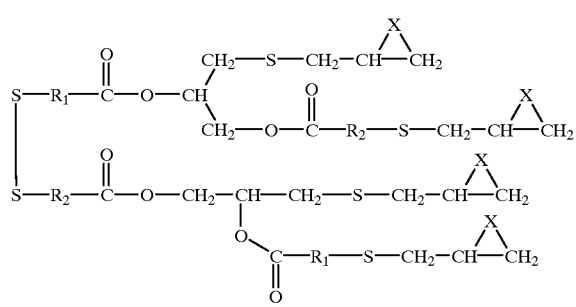

(viii)

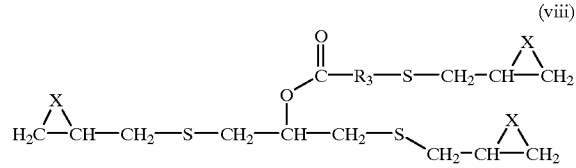

(ix)

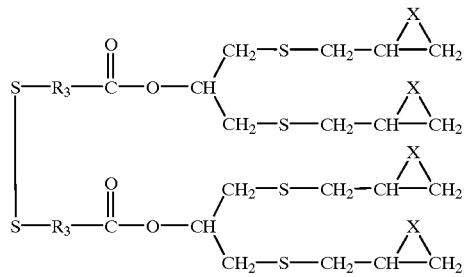

(x)

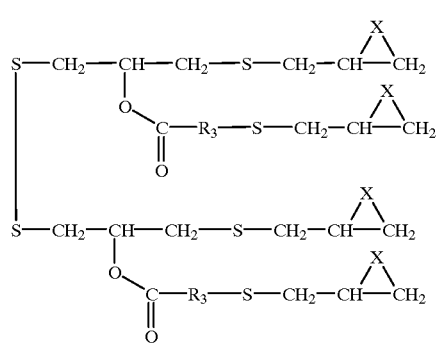

(xi)

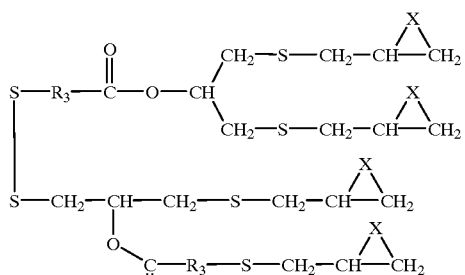

and mixtures of at least two of (i), (ii), (iii), (iv), (v), (vi), (vii), (viii), (ix), (x) and (xi);

wherein X is selected from S and O the number of functional groups (i.e., functional groups represented by the following general formula I,

wherein X is S constituting at least 50 percent of the total number of such functional groups present in said polyfunctional thiirane; and $R_1$, $R_2$ and $R_3$ are each selected independently for each general formula from the group consisting of straight or branched chain alkylene (usually containing from 1 to 20 carbon atoms, e.g., 1 to 10 carbon atoms, preferably 1 to 4 carbon atoms and more preferably 1 to 2 carbon atoms), cyclic alkylene (usually containing from 5 to 8 carbon atoms), phenylene and $C_1$–$C_9$ alkyl substituted phenylene.

In accordance with the present invention, there is further provided a polymerizable composition comprising the polyfunctional thiirane as described above. In accordance with an embodiment of the present invention, a polymerizate of the polymerizable composition of the present invention has a refractive index of at least 1.6 (as determined in accordance with American Standard Test Method (ASTM) number D 542-95), and an Abbe number of at least 27 (as determined using an instrument, such as a Bausch & Lomb ABBE-3L Refractometer).

Unless otherwise indicated, all numbers or expressions referring to quantities of ingredients, reaction conditions, etc. used herein are to be understood as modified in all instances by the term "about."

DETAILED DESCRIPTION OF THE INVENTION

While the functional groups of the polyfunctional thiirane of the present invention are preferably all thiirane groups, the polyfunctional thiirane may also contain epoxide groups. With reference to general formulas (i) through (xi), the polyfunctional thiirane of the present invention typically contains at least 50 percent of groups represented by general formula I wherein X is S, more typically at least 70 percent, preferably at least 90 percent, and more preferably 100 percent, based on the total number of functional groups of general formula I present in the polyfunctional thiirane or mixture of polyfunctional thiiranes. For example, the polyfunctional thiirane represented by general formula (i) may contain either two thiirane groups and one epoxide group, or preferably three thiirane groups.

The polyfunctional thiirane of the present invention may be prepared by art-recognized methods in which, for example, a polyfunctional epoxide intermediate is first formed from the reaction of a polythiol starting material and an epihalohydrin, e.g., epichlorohydrin. The epoxide groups of the polyfunctional epoxide intermediate are then converted to thiirane groups by reaction with a sulfurizing agent, e.g., thiocyanate, thiourea, triphenylphosphine sulfide or 3-methylbenzothiazole-2-thione, thereby forming the polyfunctional thiirane of the present invention. Typically, the sulfurizing agent used is either thiocycanate or thiourea. As the sulfurization reaction is not always 100 percent complete, some epoxide groups may not be converted to thiirane groups, and accordingly the resulting polyfunctional thiirane of the present invention may contain some epoxide groups, as described previously herein with reference to X of general formulas (i) through (xi).

Alternatively, the polyfunctional thiirane of the present invention may be prepared more directly in an art-recognized single step process that does not require a sulfurization step. In the single step process, the polyfunctional thiirane is formed from the reaction of a polythiol starting material with a 1-halo-2,3-ethylene sulfide, e.g., 1-chloro-2,3-ethyelene sulfide.

Each of the polyfunctional thiiranes represented by general formulas (i) through (xi) may be prepared as described previously herein from a corresponding polythiol starting material. For example, the polythiol starting materials that are reacted with either an epihalohydrin or 1-halo-2,3-ethylene sulfide in the preparation of the polyfunctional thiiranes represented by general formulas (i) and (viii), may be represented by the following general formulas II and III respectively,

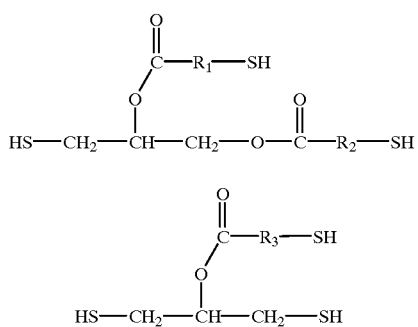

wherein $R_1$, $R_2$ and $R_3$ are as described previously herein.

The polythiol starting materials represented by general formulas II and III may be prepared by methods known in the art, for example, from an esterification or transesterification reaction between 3-mercapto-1,2-propanediol or 1,3-dimercapto-2-propanol respectively, and a thiol functional carboxylic acid or carboxylic acid ester in the presence of a strong acid catalyst, e.g., methane sulfonic acid, with the concurrent removal of water or alcohol from the reaction mixture. The preparation of polythiol starting materials represented by general formulas I and II is described in further detail in U.S. Pat. No. 5,973,192, the disclosure of which is incorporated herein by reference in its entirety. As used herein, the polythiols described and named with reference to general formulas II and III (e.g., thioglycerol bis(2-mercaptoacetate) and 1,3-dimercapto-2-propanol mercaptoacetate) is meant to include also any related co-product oligomeric species and polythiol compositions containing residual starting materials.

The polythiol starting materials represented by general formulas II and III may each be separately subjected to an oxidative coupling reaction in the presence of a suitable oxidizing agent, such as a peroxide, to form dimers containing disulfide linkages. The polythiol starting material of general formula II may be subjected to an oxidative coupling reaction to form the polythiol starting materials for each of the polyfunctional thiiranes represented by general formulas (ii) through (vii). The polythiol starting materials corresponding to each of the polyfunctional thiiranes represented by general formulas (ix) through (xi) may be prepared by subjecting the polythiol starting material represented by general formula III to an oxidative coupling reaction.

Typically, when either of the polythiol starting materials represented by general formulas II or III are subjected to an oxidative coupling reaction, a mixture of uncoupled polythiol, polythiol dimers and polythiol oligomers results. The mixture may be resolved into separate polythiol starting materials by art recognized methods, or used as a mixture of polythiol starting materials from which a mixture of polyfunctional thiiranes may be prepared. In addition, preparation of the polythiol starting materials represented by general formulas II and III can itself result in the formation of coproduct polythiol dimers and oligomers. Accordingly, each of the polyfunctional thiiranes represented by general formulas (i) through (xi) is meant to include also any related co-product oligomeric species and polyfunctional thiirane compositions containing residual starting materials.

With further reference to general formulas (i) through (xi) $R_1$, $R_2$ and $R_3$ are typically selected independently for each structure from $C_1$–$C_{20}$ linear or brached chain alkylene. In a preferred embodiment of the present invention, $R_1$, $R_2$ and $R_3$ are selected independently for each structure from methylene and ethylene.

Polymerizable compositions according to the present invention comprise one or more of the novel polyfunctional thiiranes represented by general fromuals (i)–(xi). The polmerizable composition may optionally further comprise additional monomers selected from: (a) at least one second polyfunctional thiirane; (b) at least one monofunctional thiirane; (c) at least one polythiol monomer; (d) at least one cyclic anhydride monomer; (e) epoxide monomers having at least one epoxide group; (f) ethylenically unsaturated cationically polymerizable monomers having at least one ethylenically unsaturated group; and mixtures thereof. The novel polyfunctional thiirane of the present invention may be present in the polymerizable composition in an additive amount, e.g., less than or equal to 5 percent by weight, based on the total weight of monomers, a minor amount, e.g., in an amount of less than or equal to 49 percent by weight, based on the total weight of monomers, or a major amount, e.g., in an amount of from 51 percent by weight to 100 percent by weight, based on the total weight of monomers present in the polymerizable composition.

When the novel polyfunctional thiirane of the present invention is present in the polymerizable composition in an amount of less than 100 percent by weight, based on the total weight of monomers, the balance may be composed of one or more of those classes of optional monomers as recited previously herein. For example, one or more of those previously recited classes of optional monomers may be present in the polymerizable composition in additive amounts, e.g., less than or equal to 5 percent by weight, based on the total weight of monomers; minor amounts, e.g., in an amount of less than or equal to 49 percent by weight, based on the total weight of monomers; or major amounts, e.g., in an amount of from 51 percent by weight to 99 percent by weight, based on the total weight of monomers present in the polymerizable composition.

The polymerizable composition may be polymerized by heating in the optional presence of a thermal polymerization catalyst. Classes of catalysts that may be used in the thermal polymerization of the polymerizable composition of the present invention include, for example, amines, phosphines, mineral acids, Lewis acids and carboxylic acids. Examples of amine catalysts include, primary amines, e.g., ethylamine, n-propyl amine, iso-propyl amne, n-butyl amine and tert-butyl amine; primary polyamines, e.g., ethylenediamine, 1,2-diaminopropane, 1,3-diaminopropane and 1,2-diaminobutane; secondary amines, e.g., diethylamine, dipropylamine and di-n-butylamine; tertiary amines, e.g., trimethylamine, triethylamine and tri-n-propylamine; and tertiary polyamines, e.g., tetramethylethylenediamine, pyrazine and N,N'-dimethylpiperazine. Additional amine catalysts that may be used in the polymerizable composition of the present invention are described in U.S. Pat. No. 5,945,504 at column 7, line 49 through column 9, line 35, which disclosure is incorporated herein by reference.

Phosphines that may be used as thermal polymerization catalysts in the polymerizable composition include, for example, trimethylphosphine, triethylphosphine, tri-isopropylphosphine and triphenylphosphine. Additional examples of phosphines that may be used in polymerizable composition are described in U.S. Pat. No. 5,945,504 at column 9, lines 42 through 52, which disclosure is incorporated herein by reference. Mineral acids that may be used as thermal polymerization catalysts in the polymerizable composition include, for example, sulfuric acid, nitric acid, phosphoric acid, carbonic acid and half esters thereof. Examples of Lewis acids that may be used as thermal polymerization catalysts in the polymerizable composition include, boron trihalides, such as boron trifluoride. Thermal polymerization catalysts are typically present in the polymerizable composition in at least a catalytic amount, e.g., in an amount of from 0.001 percent by weight to 5 percent by weight, based on the total weight of monomers present in the composition.

In an alternative embodiment of the present invention, the polymerizable composition is polymerized cationically by exposure to actinic radiation, in which case the composition further comprises an actinic radiation activated cationic polymerization initiator The actinic radiation activated cationic polymerization initiator is converted into an activated cationic polymerization initiator upon exposure to actinic radiation. In an embodiment of the present invention, the actinic radiation activated cationic polymerization initiator is selected from onium salts having an onium cation complex and a halide anion complex.

Onium salts that are useful as actinic radiation activated cationic polymerization initiators in the present invention include those represented by the following general formula IV,

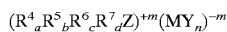

wherein $(R^4_a R^5_b R^6_c R^7_d Z)^{+m}$ is an onium cation complex of the onium salt; Z is selected from S, Se, Te, P, As, Sb, Bi, O, I, Br, Cl and N≡N; $R^4$, $R^5$, $R^6$ and $R^7$ are each selected independently from aliphatic groups, cycloaliphatic groups and aromatic groups; a, b, c and d are each independently an integer from 0 to 3, provided that the sum of a+b+c+d is equal to the valence of Z; $(MY_n)^{-m}$ is a halide anion complex of said onium salt; M is selected from B, P, As, Sb, Fe, Sn, Bi, Al, Ca, In, Ti, Zn, Sc, V, Cr, Mn and Co; Y is a halide (e.g., F, Cl, Br and I); n is equal to the valence of M; and m is the charge of the onium cation complex and the halide anion complex.

The onium cation complex of the onium salt represented by general formula IV is preferably selected from aromatic onium cation complexes, in which case $R^4$, $R^5$, $R^6$ and $R^7$ are each selected independently from aromatic groups. Preferred classes of aromatic onium cation complexes include, aromatic iodoniums and aromatic sulphoniums. In an embodiment of the present invention, the onium cation complex of onium salt initiator is selected from diphenyliodonium, 4-methoxydiphenyliodonium, bis(4-methylphenyl)iodonium, bis(4-tert-butylphenyl)iodonium, bis(dodecylphenyl)-iodonium, triphenylsulfonium and diphenyl-4-thiophenoxy-phenylsulfonium; and the halide anion complex of the onium salt initiator is selected from tetrafluoroborate ($BF_4^-$), hexafluorophosphate ($PF_6^-$), hexafluoroantimonate ($SbF_6^-$), hexafluoroarsenate ($AsF_6^-$) and hexacloroantimonate ($SbCl_6^-$). Additional examples of halide anion complexes include, perchloric acid ion ($ClO_4^-$), trifluoromethane sulfonate ion ($CF_3SO_3^-$), fluorosulfonate ion ($FSO_3^-$), toluene sulfonate ion, trinitrobenzene sulfonate ion, and trinitrotoluene sulfonate ion.

The actinic radiation activated cationic polymerization initiator is typically present in the polymerizable composition in at least an initiating amount, i.e., an amount that is at least sufficient to initiate cationic polymerization of the polymerizable composition upon exposure to actinic radiation (e.g., in an amount of from 0.001 percent by weight to 5 percent by weight, based on the total weight of monomers present in the composition). In an embodiment of the present invention, the amount of thermal polymerization catalyst or actinic radiation activated cationic polymerization initiator should be adequate to produce a polymerizate having a 15 second Barcol hardness of at least 1, preferably at least 4, e.g., from 4 to 35 (as determined in accordance with ASTM No. D 2583-95).

The polymerizable composition may further comprise at least one second polyfunctional thiirane having at least two thiirane groups, which is different than the novel polyfunctional thiiranes represented by general formulas (i)–(xi). The second polyfunctional thiirane may have a back bone structure selected from a linear or branched aliphatic backbone structure, a cycloaliphatic backbone structure, a heterocyclic backbone structure, an aromatic backbone structure and combinations thereof. The backbone structure of the second polyfunctional thiirane may optionally contain linkages selected from oxide (ether) linkages (—O—); sulfide (thioether) linkages (—S—); sulfone linkages (—(O)S(O)—); ketone linkages (—C(O)—); ester linkages (—C(O)—O—); amino linkages (e.g., —NH— and —N(R')— where R' is an aliphatic, cycloaliphatic or aromatic group); amide linkages (—C(O)—NH— and —C(O)—N<); urethane linkages (—NH—C(O)—O—); thiourethane linkages (—NH—C(O)—S—); thiocarbamate linkages (—NH—C(S)—O—); dithiourethane linkages (—NH—C(S)—S—); urea linkages (—NH—C(O)—NH—); thiourea linkages (—NH—C(S)—NH—) and combinations thereof. Typically, the backbone structure of the second polyfunctional thiirane contains linkages selected from oxide linkages, sulfide linkages and combinations thereof.

Examples of polyfunctional thiiranes having linear or branched aliphatic substantially carbon skeleton backbone structure (i.e., the backbone being substantially free of those optional linkages as recited previously herein, e.g., oxide and sulfide linkages), from which the second polyfunctional thiirane may be selected, include, but are not limited to 1,1-bis(epithioethyl)methane, 1-(epithioethyl)-1-(β-epithiopropyl)-methane, 1,1-bis(β-epithiopropyl)methane, 1-(epithioethyl)-1-(β-epithiopropyl)-ethane, 1,2-bis(β-epithiopropyl)ethane, 1-(epithioethyl)-3-(β-epithiopropyl) butane, 1,3-bis(β-epithiopropyl)propane, 1-(epithioethyl)-4-(β-epithiopropyl)pentane, 1,4-bis(β-epithiopropyl)butane, 1-(epithioethyl)-5-(β-epithiopropyl)hexane, tetrakis(β-epithiopropyl)methane and 1,1,1-tris(β-epithiopropyl) propane. Examples of polyfunctional thiiranes having cycloaliphatic substantially carbon skeleton backbone structure, from which the second polyfunctional thiirane may be selected, include, but are not limited to 1,3-and 1,4-bis(epithioethyl)cyclohexanes, 1,3-and 1,4-bis(β-epithiopropyl)cyclohexanes, bis[4-(epithioethyl) cyclohexyl]methane, bis[4-(β-epithiopropyl)cyclohexyl] methane, 2,2-bis[4-(epithioethyl)cyclohexyl]propane, 2,2-bis[4-(β-epithiopropyl)cyclohexyl]propane. Polyfunctional thiiranes having aromatic substantially carbon skeleton backbone structure, from which the second polyfunctional thiirane may be selected, include, but are not limited to, 1,3-and 1,4-bis(epithioethyl)benzenes, 1,3-and 1,4-bis(β-epithiopropyl)benzenes, bis[4-(epithioethyl)phenyl] methane, bis[4-(β-epithiopropyl)phenyl]methane, 2,2-bis[4-(epithioethyl)phenyl]propane, 2,2-bis[4-(β-epithiopropyl) phenyl]propane, 4,4'-bis(epithioethyl)biphenyls, and 4,4'-bis(β-epithiopropyl)biphenyls.

Polyfunctional thiiranes having linear or branched aliphatic backbone structure and oxide linkages that are useful in the present invention as second polyfunctional thiiranes, include, but are not limited to bis(β-epithiopropyl)ether, bis(β-epithiopropyloxy)methane, 1,2-bis(β-epithiopropyloxy)ethane, 1,3-bis(β-epithiopropyloxy) propane, 1,2-bis(β-epithiopropyloxy)propane, 1-(β-epithiopropyloxy)-2-(β-epithiopropyloxymethyl)propane, 1,4-bis(β-epithiopropyloxy)butane, 1,5-bis(β-epithiopropyloxy)pentane, tetrakis(β-epithiopropyloxymethyl)methane and 1,1,1-tris(β-epithiopropyloxymethyl)propane. Polyfunctional thiiranes having cycloaliphatic backbone structure and oxide linkages that are useful in the present invention as second polyfunctional thiiranes, include, but are not limited to bis(β-epithiopropyloxy)cyclohexanes, bis(β-epithiopropyloxymethyl)cyclohexanes, bis[4-(β-epithiopropyloxy)cyclohexyl]methane, 2,2-bis[4-(β-epithiopropyloxy)cyclohexyl]propane and bis[4-(β-epithiopropyloxy)cyclohexyl]sulfide. Examples of polyfunctional thiiranes having aromatic backbone structure and oxide linkages that are useful in the present invention as second polyfunctional thiiranes, include, but are not limited to bis(β-epithiopropyloxy)benzenes, bis(β-epithiopropyloxymethyl)benzenes, bis[4-(β-epithiopropyloxy)phenyl]methane, 2,2-bis[4-(β-epithiopropyloxy)phenyl]propane, 4,4'-bis(β-epithiopropyloxy)biphenyl, bis[4-(β-epithiopropyloxy) phenyl]sulfide, bis[4-β-epithiopropyloxy)phenyl]sulfone and 4,4'-bis(β-epithiopropyloxy)benzophenone.

Polyfunctional thiiranes having linear or branched aliphatic backbone structure and sulfide linkages that are useful in the present invention as second polyfunctional thiiranes, include, but are not limited to bis(β-epithiopropyl)sulfide, bis(β-epithiopropylthio)methane, 1,2-bis(β-epithiopropylthio)ethane, 1,3-bis(β-epithiopropylthio) propane, 1,2-bis(β-epithiopropylthio)propane, 1-(β-epithiopropylthio)-2-(β-epithiopropylthiomethyl)propane, 1,4-bis(β-epithiopropylthio)butane, 1,3-bis(β-epithiopropylthio)butane, 1,5-bis(β-epithiopropylthio) pentane, tetrakis(β-epithiopropylthiomethyl)methane and 1,1,1-tris(β-epithiopropylthiomethyl)propane. Further examples of polyfunctional thiiranes having linear or branched aliphatic backbone structure and sulfide linkages, that may be used in the present invention as second polyfunctional thiiranes, are described in U.S. Pat. No. 5,807,975 at column 3, line 1 through column 7, line 50, which disclosure is incorporated herein by reference.

Polyfunctional thiiranes having cycloaliphatic backbone structure and sulfide linkages that are useful in the present invention as second polyfunctional thiiranes, include, but are not limited to bis(β-epithiopropylthio)cyclohexanes, bis(β-epithiopropylthiomethyl)cyclohexanes, bis[4-(β-epithiopropylthio)cyclohexyl]methane, 2,2-bis[4-(β-epithiopropylthio)cyclohexyl]propane, bis[4-(β-epithiopropylthio)cyclohexyl]sulfide, bis[4-(β-epithiopropyl)-cyclohexyl]sulfide, and bis[4-(epithioethylcyclohexyl]sulfide. Examples of polyfunctional thiiranes having aromatic backbone structure and sulfide linkages that are useful in the present invention as second polyfunctional thiiranes, include, but are not limited to bis(β-epithiopropylthio)benzenes, bis(β-epithiopropylthiomethyl)benzenes, bis[4-(β-epithiopropylthio)phenyl]methane, 2,2-bis[4-(β-epithiopropylthiopropylthio)phenyl]propane, bis[4-(β-epithiopropylthio)phenyl]sulfide, bis[4-(β-epithiopropylthio)phenyl]sulfone, 4,4'-bis(β-epithiopropylthio)biphenyl, bis[4-(epithioethyl)phenyl] sulfide, bis[4-(β-epithiopropyl)phenyl]sulfide and 4,4'-bis (β-epithiopropylthio)benzophenone. Polyfunctional thiiranes having aromatic backbone structure and sulphone linkages include, for example, bis[4-(epithioethyl)phenyl] sulfone and bis[4-(β-epithiopropyl)phenyl]sulfone.

Second polyfunctional thiiranes useful as second polyfunctional thiiranes in the polymerizable composition of the present invention may have heterocyclic backbone structure containing, for example, oxygen, sulfur, nitrogen and/or silicon atoms. Heterocyclic backbone structures containing sulfur atoms are preferred. A preferred class of heterocyclic backbone structure is dithiane backbone structure, and in particular 1,4-dithiane backbone structure. Examples of polyfunctional thiiranes having 1,4-dithiane backbone structure that may be used in the present invention include, but are not limited to, 2,5-bis(epithioethyl)-1,4-dithane, 2,5-bis (β-epithiopropyl)-1,4-dithiane, 2,5-bis(β-epithiopropyloxymethyl)-1,4-dithiane, 2,5-bis(β-epithiopropyloxyethyloxymethyl)-1,4-dithiane, 2,5-bis(β-epithiopropylthiomethyl)-1,4-dithiane and 2,5-bis(β-epithiopropylthioethylthiomethyl)-1,4-dithiane. Additional examples of useful polyfunctional thiiranes having 1,4-dithiane backbone structure are described in U.S. Pat. No. 5,945,504 at column 3, line 40 through column 5, line 14, which disclosure is incorporated herein by reference.

Polyfunctional thiiranes having backbone linkages selected from urethane linkages, thiourethane linkages, thiocarbamate linkages, dithiourethane linkages, urea linkages, thiourea linkages and combinations thereof may be prepared according to methods that are known to those of ordinary skill in the art. Typically, an intermediate having active hydrogen group functionality is formed from the combination of (1) a first reactant having two or more active hydrogen groups selected from hydroxyl, thiol, primary amine, secondary amine and combinations thereof, and (2) a second reactant having at least two functional groups selected from isocyanate (—NCO), isothiocyanate (—NCS)

and combinations thereof (i.e., a polyiso(thio)cyanate). The equivalents ratio of the active hydrogen groups of the first reactant to the iso(thio)cyanate groups of the second reactant is selected such that the intermediate product of the combination is active hydrogen group functional, e.g., having hydroxyl or thiol functionality. The active hydrogen group functional intermediate may then be further reacted with an epihalohydrin to form a polyfunctional epoxide intermediate, which is then converted to a polyfunctional thiirane by reaction with a sulfurizing agent, as described previously herein. Alternatively the active hydrogen group functional intermediate may be reacted with a 1-halo-2,3-ethylene sulfide to form a polyfunctional thiirane, as described previously herein.

In the preparation of second polyfunctional thiiranes having backbone linkages selected from urethane linkages, thiourethane linkages, thiocarbamate linkages, dithiourethane linkages, urea linkages, thiourea linkages and combinations thereof, the first reactant having two or more active hydrogen groups selected from hydroxyl, thiol, primary amine, secondary amine and combinations thereof may be selected from those that are known to the skilled artisan.

Examples of polyols that may be reacted with polyiso(thio)cyanates in the preparation of second polyfunctional thiiranes useful in the present invention, include, but are not limited alkylene glycols, e.g., ethylene glycol and propylene glycol; di- through penta(alkylene glycols), e.g., di- through penta(ethylene glycol) and di- through penta(propylene glycol); poly(alkylene glycols) having more than 5 repeat units, e.g., poly(ethylene glycol); block copolymers of poly(alkylene glycols), e.g., poly[(ethylene glycol)-b-(propylene glycol)-b-(ethylene glycol)]; linear or branched alkyl polyols, e.g., 1,3-propane diol, 1,4-butane diol, 1,6-hexane diol, neopentyl glycol, glycerol, trimethylol propane, trimethylol ethane, pentaerythritol, di-trimethylol propane and di-pentaerythritol; cycloalkyl polyols, e.g., cyclohexane dimethanols, hydrogenated bisphenol A and alkylene oxide extended hydrogenated bisphenol A; aromatic polyols, e.g., dimethylol benzene, catechol, resorcinol, bisphenol A, bisphenol sulfone, bisphenol ether, bisphenol sulfide, 4,4'-dihydroxy-benzophenone and halogenated bisphenol A; and N,N-hydroxyalkylamides, e.g., N,N-2-hydroxyethylacetamide and bis(N,N-2-hydroxyethyl) adipamide. Polythiols that may be reacted with polyiso(thio)cyanates in the preparation of polyfunctional thiiranes useful in the present invention, include, polythiols corresponding to those polyols as recited previously herein, e.g., 4,4'-dimercapto-benzophenone, and those polythiols as recited further herein.

Polyfunctional primary amines that may be reacted with polyiso(thio)cyanates in the preparation of polyfunctional thiiranes useful in the present invention, include, but are not limited to, linear or branched aliphatic polyamines, e.g., alkylene diamines, such as 1,2-ethylene diamine and 1,3-diaminopropane; cycloaliphatic polyamines, e.g., bisaminocyclohexanes, bisaminomethylcyclohexanes and isophoronediamine; and aromatic polyamines, e.g., xylylenediamines, tolylenediamines and phenylenediamines. Examples of polyfunctional secondary amines that may be reacted with polyiso(thio)cyanates in the preparation of polyfunctional thiiranes useful in the present invention, include, but are not limited to, N,N'-dialkyl-diaminoalkanes, e.g., N,N'-dimethylethylenediamine, N,N'-dimethyl-1,3-diaminopropane and N,N'-diethyl-1,3-diaminopropane. Examples of materials having both primary amines and secondary amines include, ethyleneamines, such as diethylenetriamine, triethylenetetramine, tetraethylenepentamine and pentaethylenehexamine.

Polyiso(thio)cyanates that may be used to prepare second polyfunctional thiiranes having backbone linkages selected from urethane linkages, thiourethane linkages, thiocarbamate linkages, dithiourethane linkages, urea linkages, thiourea linkages and combinations thereof, may be selected from those that are known to the skilled artisan, e.g., toluene diisocyanate, isophorone diisocyanate, 1,2-diisothiocyanatoethane and 1-isocyanato-4-isothiocyanatocyclohexane. Examples of suitable poly(isocyanate), poly(isothiocyanate) and poly(isocyanate-isothiocyanate) reactants that may be used to prepare second polyfunctional thiiranes are described in U.S. Pat. No. 5,932,681 at column 5, line 60 through column 8, line 62, which disclosure is incorporated herein by reference.

In an embodiment of the present invention, the second polyfunctional thiirane is selected from polyfunctional thiiranes having at least one fused ring epithio group, e.g., a thiabicyclo group. Examples of polyfunctional thiiranes having at least one fused ring epithio group from which the second polyfunctional thiirane may be selected include, but are not limited to, 7-thiabicyclo[4.1.0]hept-3-ylmethyl 7-thiabicyclo[4.1.0]heptane-3-carboxylic acid ester, 4-methyl-7-thiabicyclo[4.1.0]hept-3-ylmethyl 4-methyl-7-thiabicyclo[4.1.0]heptane-3-carboxylic acid ester, 3-(epithioethyl)-7-thiabicyclo[4.1.0]heptane, 2-(epithioethyl)-7-thiabicyclo[4.1.0]heptane, 3-(2,3-epithiopropyl)-7-thiabicyclo[4.1.0]heptane, 1-methyl-4-(2-methylthiiranyl)-7-thiabicyclo[4.1.0]heptane, 4,8-dithiatricyclo[5.1.0.0$^{3,5}$]octane, 3,8-dithiatricyclo[5.1.0.0$^{2,4}$]octane, 3-oxa-6,9-dithiatetracyclo[6.1.0.0 $^{2,4}$.0$^{5,7}$]nonane, 3,6,9-trithiatetracyclo[6.1.0.0$^{2,4}$.0$^{5,7}$]nonane, 5,10-dithiatricyclo[7.1.0.0$^{4,6}$]decane and mixtures thereof. A preferred second polyfunctional thiirane is 7-thiabicyclo[4.1.0]hept-3-ylmethyl 7-thiabicyclo[4.1.0]heptane-3-carboxylic acid ester.

The polymerizable composition of the present invention may optionally further comprise a monofunctional thiirane having a single thiirane group. Examples of monofunctional thiiranes that may be present in the polymerizable composition include, but are not limited to, 1,2-propylene sulfide; 1-halo-2,3-propylene sulfide, e.g., 1-chloro-2,3-propylene sulfide; thioglycidyl esters of monocarboxylic acids, e.g., thioglycidyl acetic acid ester, thioglycidyl propionic acid ester and thioglycidyl benzoic acid ester; thioglycidyl ethers, e.g., methyl thioglycidyl ether, ethyl thioglycidyl ether, propyl thioglycidyl ether and butyl thioglycidyl ether; $C_5$–$C_{12}$ cycloalkylene sulfides, e.g., 6-thiabicyclo[3.1.0] hexane (cyclopentene sulfide), 7-thiabicyclo[4.1.0]heptane (cyclohexene sulfide), 8-thiabicyclo[5.1.0]octane (cycloheptene sulfide), 9-thiabicyclo[6.1.0]nonane (cyclooctene sulfide) and 11-thiabicyclo[8.1.0]undecane (cyclodecene sulfide); and mixtures of such monofunctional thiiranes.

The polymerizable composition of the present invention may yet further optionally comprise a polythiol having at least two thiol groups. Examples of polythiols that may be optionally present in the polymerizable composition include, but are not limited to, 2,2'-thiodiethanethiol, pentaerythritol tetrakis(3-mercaptopropionate), pentaerythritol tetrakis(2-mercaptoacetate), trimethylolpropane tris(3-mercaptopropionate), trimethylolpropane tris(2-mercaptoacetate), 4-mercaptomethyl-3,6-dithia-1,8-octanedithiol, 4-tert-butyl-1,2-benzenedithiol, 4,4'-thiodibenzenethiol, benzenedithiol, ethylene glycol di(2-mercaptoacetate), ethylene glycol di(3-mercaptopropionate), poly(ethylene glycol) di(2-mercaptoacetate) and poly(ethylene glycol) di(3- mercaptopropionate) polythiol monomers represented by general formula II, polythiol monomers represented by general formula III, and mixtures thereof.

The polymerizable composition may optionally further comprise one or more cyclic anhydride monomers. Preferably, the cyclic anhydride monomer is present in the polymerizable composition together with the polythiol monomer. As used herein and in the claims, the term "cyclic anhydride" refers to those materials in which the anhydride group is part of a cyclic ring. Examples of cyclic anhydrides that may be used in the present invention include, but are not limited to, phthalic anhydride, tetrahydrophthalic anhydride, hexahydrophthalic anhydride, hexahydromethylphthalic anhydride, maleic anhydride, citraconic anhydride, itaconic anhydride, chlorendic anhydride, methyl-5-norbornene-2,3-dicarboxylic anhydride, endo-bicyclo[2.2.2]oct-5-ene-2,3-dicarboxylic anhydride and pyromellitic dianhydride. The cyclic anhydride may contain halogen groups, e.g., chlorine and/or bromine groups, examples of which include halogenated derivatives of those cyclic anhydrides as recited previously herein. Preferred cyclic anhydrides include phthalic anhydride, methyl-5-norbornene-2,3-dicarboxylic anhydride and mixtures of phthalic anhydride and methyl-5-norbornene-2,3-dicarboxylic anhydride. If used, the cyclic anhydride is typically present in the polymetizable composition in an amount of less than 20 percent by weight, based on the total weight of polymerizable monomers, more typically in an amount of less than 10 percent by weight, based on the total weight of polymerizable monomers.

Epoxide monomers having at least one epoxide group may also optionally be present in the polymerizable composition of the present invention. The optional epoxide monomer is free of thiirane groups and is different than the polyfunctional thiiranes represented by general formulas (i)–(xi), and the second polyfunctional thiirane. Examples of epoxide monomers that may be present in the polymerizable composition include epoxides corresponding to those polyfunctional and monofunctional thiiranes as recited previously herein.

One or more ethylenically unsaturated cationically polymerizable monomers may also optionally be present in the polymerizable composition. Classes of ethylenically unsaturated cationically polymerizable monomers that may be used include vinyl ethers, vinyl functional aromatic monomers and olefins. Vinyl ethers that may be present in the polymerizable composition include, for example, monofunctional vinyl ethers, such as linear or branched alkyl vinyl ethers and cycloalkyl vinyl ethers, and polyfunctional vinyl ethers, such as polyol vinyl ethers, e.g., ethylene glycol divinyl ether and trimethylolpropane trivinyl ether. Vinyl functional aromatic monomers that may be present in the polymerizable composition include, for example, styrene, divinyl benzene and trivinyl benzene. Examples of olefins that may be present in the polymerizable composition include, isobutylene and vinylcyclohexane. A preferred ethylenically unsaturated cationically polymerizable monomer is styrene.

When the polymerizable composition is used to prepare a polymerizate having a refractive index of at least 1.6, and an Abbe value of at least 27, the epoxide monomer and/or ethylenically unsaturated monomer when used are typically present in the polymerizable composition in a minor amount, e.g., in an amount totaling less than 50 percent by weight, based on the total weight of monomers present in the composition. More typically, the epoxide monomer and/or ethylenically unsaturated monomer are optionally present in the polymerizable composition in amounts totaling less than 25 percent by weight, e.g., in an amounts totaling less than 10 percent by weight, based on the total weight of monomers present in the polymerizable composition.

Various conventional additives may be incorporated with the polymerizable organic composition of the present invention. Such additives may include light stabilizers, heat stabilizers, antioxidants, ultraviolet light absorbers, mold release agents, static (non-photochromic) dyes, pigments, and flexibilizing additives that are not cationically polymerizable (e.g., alkoxylated phenol benzoates, poly(alkylene glycol) dibenzoates, and poly(alkoxylated) bisphenols). When actinic radiation activated cationic polymerization initiators are used, one or more photosensitizers may be also be added to the polymerizable composition (e.g., benzophenone, benzoin isopropyl ether and thioxanthone). Antiyellowing additives, e.g., 3-methyl-2-butenol, organo pyrocarbonates and triphenyl phosphite, may also be added to polymerizable organic compositions of the present invention to enhance resistance to yellowing. Such additives are typically present in the compositions of the present invention in amounts totaling less than 10 percent by weight, preferably less than 5 percent by weight, and more preferably less than 3 percent by weight, based on the total weight of the polymerizable composition.

The polyfunctional thiirane of the present invention, any optional monomers, e.g., monofunctional thiiranes, second polyfunctional thiiranes, polythiols, cyclic anhydrides, epoxide monomers and ethylenically unsaturated monomers, and any additives are typically mixed together in a suitable container. The thermal polymerization catalyst or actinic radiation activated cationic polymerization initiator is then added to the monomer mixture and the polymerizable composition is charged to a mold. The contents of the filled mold are then polymerized either thermally or by exposure to actinic radiation. After completion of polymerization, the polymerizate is typically removed from the mold, and may be further processed (e.g., cut, ground and/or polished) if desired. Thermal polymerization typically involves exposing the filled molds to a controlled thermal cure cycle over a period of at least one hour, e.g., from 1 to 48 hours, and using temperatures ranging from, for example, 25° C. to 200° C.

The actinic radiation used to polymerize the composition may be selected from visible light, ultraviolet (UV) light, electron beam, X-ray radiation, radio frequency radiation and combinations thereof. Preferably the actinic radiation is selected from visible light, UV light and combinations thereof. When polymerized by exposure to actinic radiation, at least a portion of the filled mold is transparent to the actinic radiation, e.g., an ophthalmic lens mold fabricated from quartz glass. The filled mold is exposed to actinic radiation (e.g., having a wavelength of from 250 to 450 nanometers) typically by passing or holding the filled mold under the actinic radiation source, e.g., mercury lamps, xenon lamps, sodium lamps and alkali metal lamps. Concurrent with or following exposure to actinic radiation, the filled mold may optionally be subjected to a thermal co- or post-cure, for example at a temperature of from 70° C. to 150° C., over a period of from 1 to 5 hours.

Polymerizates prepared from the polymerizable composition of the present invention, will be solid, and preferably transparent, e.g., suitable for optical or ophthalmic applications. In an embodiment of the present invention, the polymerizates will also have a refractive index of at least 1.6, preferably at least 1.63 and more preferably at least 1.65, and adequately high Abbe numbers, e.g., an Abbe number of at least 27. In an embodiment, the polymerizate of the present invention will have an Abbe number of at least 29. In another embodiment, the polymerizate will have an Abbe number of at least 33 or 35. Further, in an embodiment of the invention, the polymerizate of the present invention will have a 15 second Barcol hardness of at least 1. Solid articles that may be prepared from polymerizable organic compositions of the present invention include, but are not limited to, optical lenses, such as plano and ophthalmic lenses, sun lenses, windows, automotive transparencies, e.g., windshields, sidelights and backlights, and aircraft transparencies, etc.

When used to prepare photochromic articles, e.g., lenses, the polymerizate should be transparent to that portion of the electromagnetic spectrum which activates the photochromic substance(s) incorporated in the matrix, i.e., that wavelength of ultraviolet (UV) light that produces the colored or open form of the photochromic substance and that portion of the visible spectrum that includes the absorption maximum wavelength of the photochromic substance in its UV activated form, i.e., the open form. Photochromic substances that may be utilized with the polymerizates of the present invention are organic photochromic compounds or substances containing same that may be incorporated, e.g., dissolved, dispersed or diffused into such polymerizates.

A first group of organic photochromic substances contemplated for use to form the photochromic articles of the present invention are those having an activated absorption maximum within the visible range of greater than 590 nanometers, e.g., between greater than 590 to 700 nanometers. These materials typically exhibit a blue, bluish-green, or bluish-purple color when exposed to ultraviolet light in an appropriate solvent or matrix. Examples of classes of such substances that are useful in the present invention include, but are not limited to, spiro(indoline)naphthoxazines and spiro(indoline)benzoxazines. These and other classes of such photochromic substances are described in the open literature. See for example, U.S. Pat. Nos.: 3,562,172; 3,578,602; 4,215,010; 4,342,668; 5,405,958; 4,637,698; 4,931,219; 4,816,584; 4,880,667; 4,818,096. Also see for example: Japanese Patent Publication 62/195383; and the text, *Techniques in Chemistry,* Volume III, "Photochromism," Chapter 3, Glenn H. Brown, Editor, John Wiley and Sons, Inc., New York, 1971.

A second group of organic photochromic substances contemplated for use to form the photochromic articles of the present invention are those having at least one absorption maximum and preferably two absorption maxima, within the visible range of between 400 and less than 500 nanometers. These materials typically exhibit a yellow-orange color when exposed to ultraviolet light in an appropriate solvent or matrix. Such compounds include certain chromenes, i.e., benzopyrans and naphthopyrans. Many of such chromenes are described in the open literature, e.g., U.S. Pat. Nos. 3,567,605; 4,826,977; 5,066,818; 4,826,977; 5,066,818; 5,466,398; 5,384,077; 5,238,931; and 5,274,132.

A third group of organic photochromic substances contemplated for use to form the photochromic articles of the present invention are those having an absorption maximum within the visible range of between 400 to 500 nanometers and another absorption maximum within the visible range of between 500 to 700 nanometers. These materials typically exhibit color(s) ranging from yellow/brown to purple/gray when exposed to ultraviolet light in an appropriate solvent or matrix. Examples of these substances include certain benzopyran compounds, having substituents at the 2-position of the pyran ring and a substituted or unsubstituted heterocyclic ring, such as a benzothieno or benzofurano ring fused to the benzene portion of the benzopyran. Such materials are the subject of U.S. Pat. No. 5,429,774.

Other photochromic substances contemplated are photochromic organo-metal dithizonates, i.e., (arylazo)-thioformic arylhydrazidates, e.g., mercury dithizonates, which are described in, for example, U.S. Pat. No. 3,361,706. Fulgides and fulgimides, e.g. the 3-furyl and 3-thienyl fulgides and fulgimides, are described in U.S. Pat. No. 4,931,220 at column 20, line 5 through column 21, line 38.

The disclosures relating to such photochromic substances in the aforedescribed patents are incorporated herein, in their entirety, by reference. The photochromic articles of the present invention may contain one photochromic substance or a mixture of photochromic substances, as desired. Mixtures of photochromic substances may be used to attain certain activated colors such as a near neutral gray or brown.

Each of the photochromic substances described herein may be used in amounts and in a ratio (when mixtures are used) such that a polymerizate to which the mixture of compounds is applied or in which they are incorporated exhibits a desired resultant color, e.g., a substantially neutral color such as shades of gray or brown when activated with unfiltered sunlight, i.e., as near a neutral color as possible given the colors of the activated photochromic substances. The relative amounts of the aforesaid photochromic substances used will vary and depend in part upon the relative intensities of the color of the activated species of such compounds, and the ultimate color desired.

The photochromic compounds or substances described herein may be applied to or incorporated into the polymerizate by various methods described in the art. Such methods include (a) dissolving or dispersing the substance within the polymerizate, e.g., imbibition of the photochromic substance into the polymerizate by immersion of the polymerizate in a hot solution of the photochromic substance or by thermal transfer; (b) providing the photochromic substance as a separate layer between adjacent layers of the polymerizate, e.g., as a part of a polymer film or polymer layer; and (c) applying the photochromic substance as part of a coating or polymer layer placed on the surface of the polymerizate. The term "imbibition" or "imbibe" is intended to mean and include permeation of the photochromic substance alone into the polymerizate, solvent assisted transfer absorption of the photochromic substance into a porous polymer, vapor phase transfer, and other such transfer mechanisms.

The amount of photochromic substance or composition containing same applied to or incorporated into the polymerizate is not critical provided that a sufficient amount is used to produce a photochromic effect discernible to the naked eye upon activation. Generally such an effective amount can be described as a photochromic amount. The particular amount used depends often upon the intensity of color desired upon irradiation thereof and upon the method used to incorporate or apply the photochromic substances. Typically, the more photochromic substance applied to or incorporated into the polymerizate, the greater is the color intensity of the resulting photochromic article. Generally, the amount of total photochromic substance incorporated into or applied to a photochromic optical polymerizate may range from 0.15 to 0.35 milligrams per square centimeter of surface to which the photochromic substance(s) is incorporated or applied.

It is also contemplated that photochromic substances may be added to the polymerizable compositions of the present invention prior to polymerization. However, when this is done it is preferred that the photochromic substance(s) be resistant to potentially adverse interactions with the thermal catalysts, actinic radiation activated cationic polymerization initiator and/or the thiirane groups of the monomers, the thiol groups of the optional polythiol monomer and the sulfide linkages that form within the polymerizate. These adverse interactions can result in deactivation of the photochromic substance(s), e.g., by trapping them in either an open or closed form. Photochromic substances can also include photochromic pigments and organic photochromic substances encapsulated in metal oxides, the latter of which are described in U.S. Pat. Nos. 4,166,043 and 4,367,170. Organic photochromic substances sufficiently encapsulated within a matrix of an organic polymerizate, as described in U.S. Pat. No. 4,931,220, may also be incorporated into the polymerizable organic compositions of the present invention prior to curing.

The present invention is more particularly described in the following examples, which are intended to be illustrative only, since numerous modifications and variations therein will be apparent to those skilled in the art. Unless otherwise specified, all parts and all percentages are by weight.

EXAMPLES

First Trisepoxidation of TGBMA

Thioglycerol bis(2-mercaptoacetate) (TGBMA), 100 grams, was mixed with 65.6 grams (0.702 moles) of epichlorohydrin dissolved in 300 ml of toluene. The equivalent weight for TGBMA was 85; however, because TGBMA contains cyclic oligomeric sulfides, the titration results showed only 60–65% of theoretical —SH. Thus, the equivalent weight was calculated as 85/0.6=141, and 100 grams= 0.702 equivalents.

The TGBMA/epichlorhydrin mixture was cooled to a temperature of less than 0° C. A few drops of 8% NaOH solution were added slowly while maintaining the temperature. After approximately 45 minutes, a slow addition of 8% NaOH solution was initiated. The temperature did not exceed 5° C. After approximately one-half of the equivalent amount of NaOH was added, the exothermic tendency of the reaction was greatly reduced and the remainder of the NaOH was added at a faster rate. The contents were allowed to warm to room temperature overnight with stirring. The product recovered was 125 grams of a white gum. The product theoretically has the following structure.

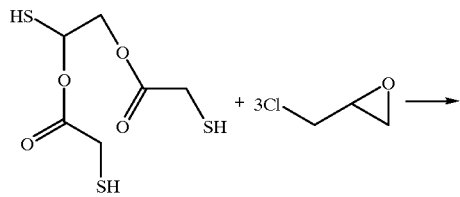

-continued

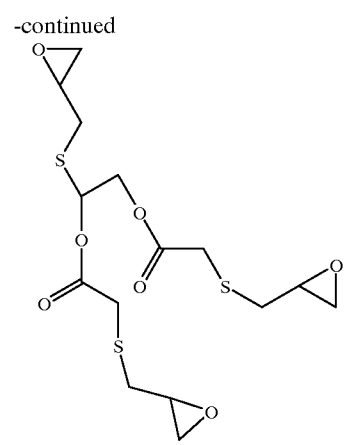

Conversion of Epoxides to Thiirane

The white gum product (25 grams; 0.144 equivalents of epoxide) was disolved in 250 grams of acetic anhydride; 15 grams (0.144 moles) of thiourea was added and the mixture was stirred. The mixture displayed a moderate exothermic reaction but the temperature was controlled at 30° C. by cooling with an ice bath. After approximately one hour, the exothermic heat evolution ended and the mixture was allowed to stir overnight. The next day a yellow solution containing a white solid was observed. The white solid was removed by filtration. A yellow, gummy solid was obtained by removal of the acetic anhydride on a rotary evaporator. The product theoretically has the following structure.

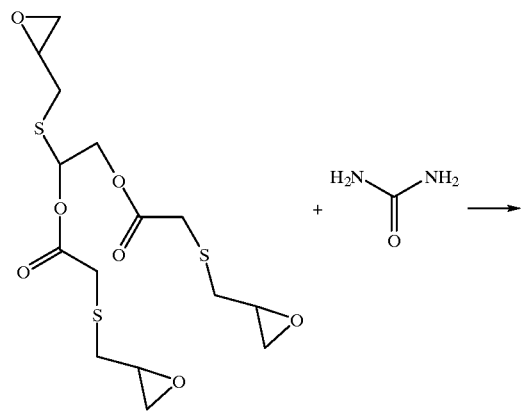

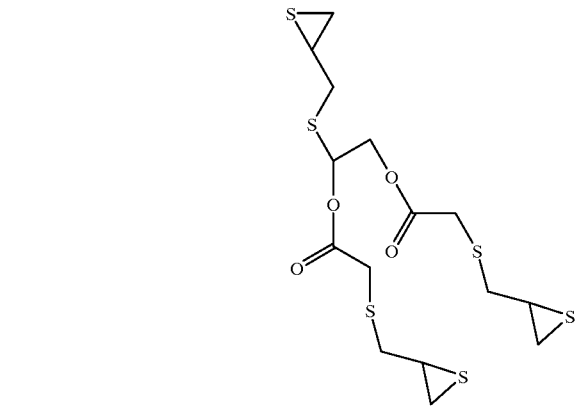

The present invention has been described with reference to specific details of particular embodiments thereof. It is not intended that such details be regarded as limitations upon the scope of the invention except insofar as and to the extent that they are included in the accompanying claims.

What is claimed is:
1. A polyfunctional thiirane selected from the group consisting of polyfunctional thiiranes represented by the following general formulas:
(i)
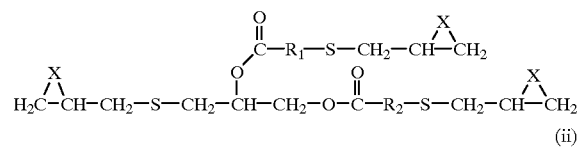
(ii)
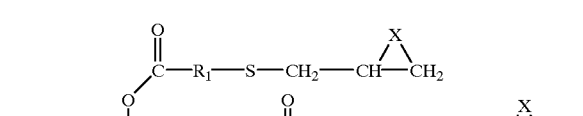
(iii)
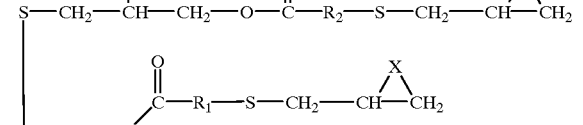
(iv)
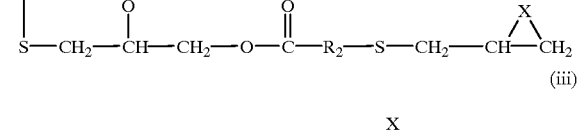
(v)
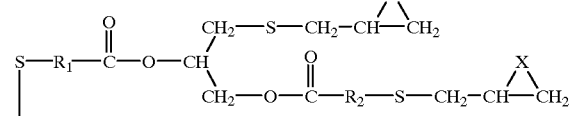
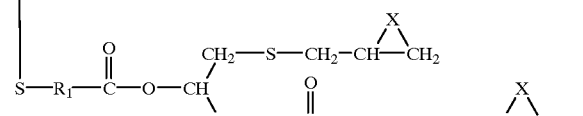
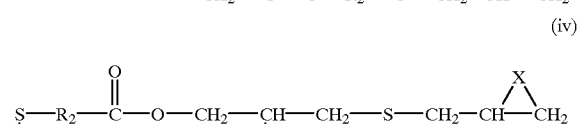
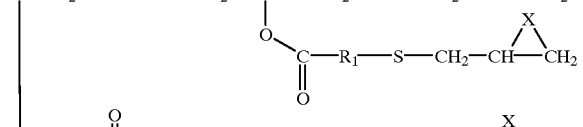
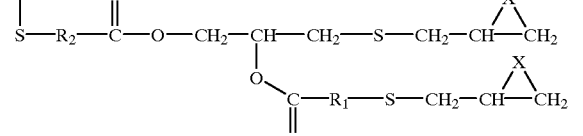
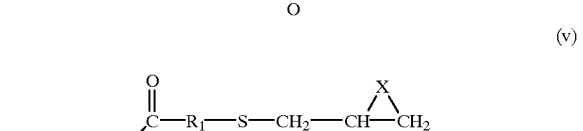
(vi)
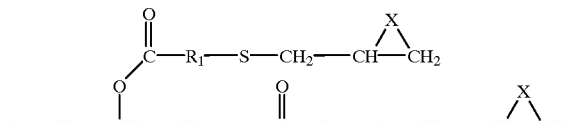
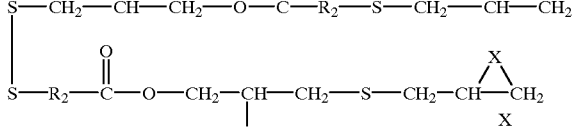
(vii)
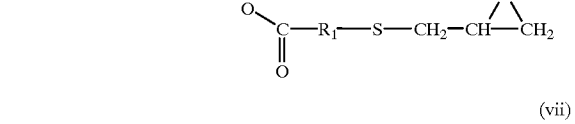
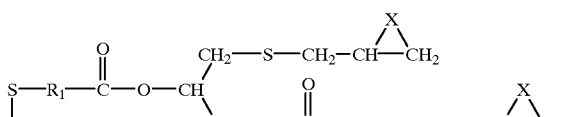
(viii)
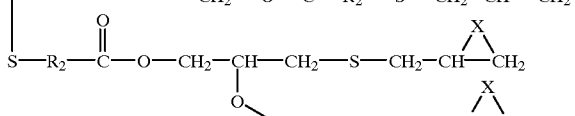
(ix)
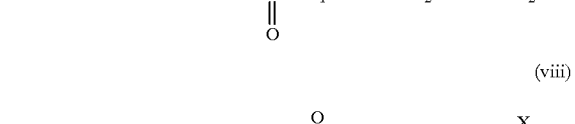
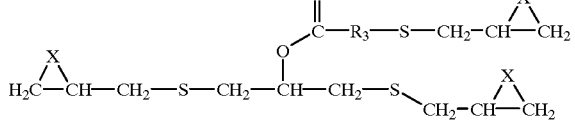
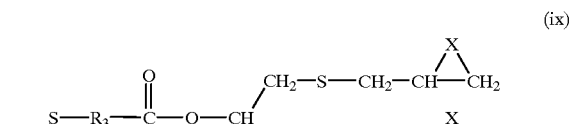
(x)
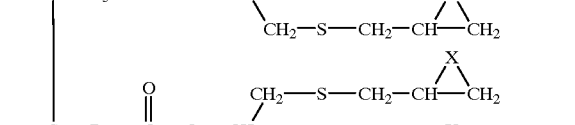
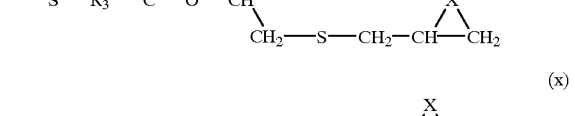
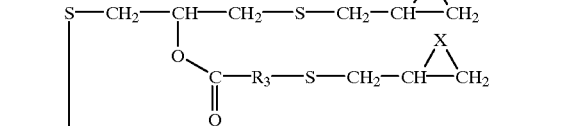
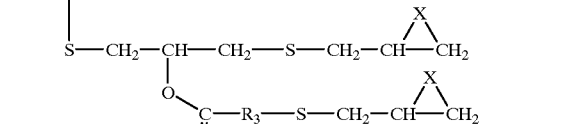

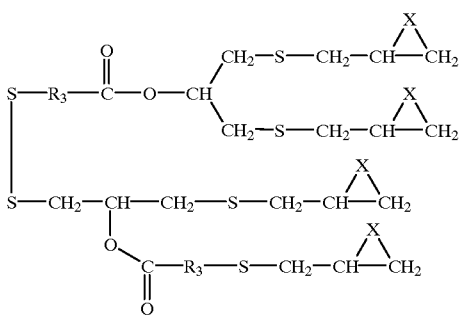

and mixtures of at least two of (i), (ii), (iii), (iv), (v), (vi), (vii), (viii), (ix), (x) and (xi);
wherein X is selected from the group consisting of S and O, the number of functional groups wherein X is S constituting at least 50 percent of the total number of such functional groups present in said polyfunctional thiirane; and $R_1$, $R_2$ and $R_3$ are each selected independently for each general formula from the group consisting of straight or branched chain alkylene, cyclic alkylene, phenylene and $C_1$–$C_9$ alkyl substituted phenylene.

2. The polyfunctional thiirane of claim 1 wherein $R_1$, $R_2$ and $R_3$ are each selected independently for each structure from straight or branched chain alkylene.

3. The polyfunctional thiirane of claim 2 wherein $R_1$, $R_2$ and $R_3$ are each selected independently from the group consisting of methylene and ethylene.

4. A polymerizable material comprising the polyfunctional thiirane of claim 1.

5. The polymerizable material of claim 4 further comprising a monomer selected from the group consisting of at least one second polyfunctional thiirane having at least two thiirane groups, which is different from the polyfunctional thiiranes of claim 1 represented by general formulas (i)–(xi); at least one monofunctional thiirane having a single thiirane group; at least one polythiol monomer; at least one cyclic anhydride monomer; an epoxide monomer having at least one epoxide group, being free of thiirane groups, and different than the polyfunctional thiiranes of claim 1 represented by general formulas (i)–(xi); an ethylenically unsaturated cationically polymerizable monomer having at least one ethylenically unsaturated group; and mixtures thereof.

6. A material obtained by heating the polymerizable material of claim 4 in the presence of a thermal polymerization catalyst.

7. The material of claim 6, wherein said thermal polymerization catalyst is selected from the group consisting of amine, phosphine, mineral acid, Lewis acid, carboxylic acid and mixtures thereof.

8. A polymerizate obtained by polymerizing the polymerizable material of claim 4, wherein said polymerizate has a 15 second Barcol hardness of at least 1.

9. A polymerizate obtained by polymerizing the polymerizable material of claim 4, wherein the polymerizate has a refractive index of at least 1.6 and an Abbe number of at least 29.

10. The polymerizate of claim 9, wherein said polymerizate has a 15 second Barcol hardness of at least 1.

11. A polymerizate obtained by polymerizing the polymerizable material of claim 4 by heating said polymerizable material in the presence of a thermal polymerization catalyst.

12. The polymerizate of claim 11 wherein said thermal polymerization catalyst is chosen from amines, phosphines, mineral acids, Lewis acids, carboxylic acids and mixtures thereof.

13. A polymerizate obtained by polymerizing the polymerizable material of claim 4, wherein the polymerizate has a refractive index of at least 1.6 and an Abbe number of at least 27.

14. The polymerizate of claim 13, wherein said polymerizate has a 15 second Barcol hardness of at least 1.

15. A photochromic article comprising:
(a) the polymerizate of claim 13; and
(b) a photochromic amount of organic photochromic substance.

16. The photochromic article of claim 15 wherein the organic photochromic substance is selected from the group consisting of spiro(indoline)naphthoxazines, spiro(indoline) benzoxazines, benzopyrans, naphthopyrans, chromenes, organo-metal dithizonates, fulgides and fulgimides and mixtures thereof.

* * * * *